United States Patent
Kuroda et al.

(10) Patent No.: US 6,515,185 B1
(45) Date of Patent: Feb. 4, 2003

(54) METHOD OF PRODUCING CYCLODODECANONE AND CYCLODODECANOL

(75) Inventors: Nobuyuki Kuroda, Ube (JP); Hiroshi Shiraishi, Ube (JP); Takato Nakamura, Ube (JP)

(73) Assignee: Ube Industries, Ltd., Ube (JP)

( * ) Notice: Subject to any disclaimer, the term of this patent is extended or adjusted under 35 U.S.C. 154(b) by 0 days.

(21) Appl. No.: 09/677,985

(22) Filed: Oct. 3, 2000

(30) Foreign Application Priority Data

Oct. 4, 1999 (JP) ........................... 11-282697
Apr. 3, 2000 (JP) ........................ 2000-100500

(51) Int. Cl.$^7$ .................. C07C 45/51; C07C 35/20; C07C 35/18; C07C 35/08
(52) U.S. Cl. .................. 568/338; 568/361; 568/821; 568/823; 568/832
(58) Field of Search .................. 568/338, 361, 568/821, 823, 832

(56) References Cited

U.S. PATENT DOCUMENTS 5,304,686 A * 4/1994 Slaugh et al.

FOREIGN PATENT DOCUMENTS

| EP | 0 192 298 | 8/1986 |
| EP | 1 018 498 | 7/2000 |
| GB | 1 273 689 | 6/1970 |

OTHER PUBLICATIONS

"Journal of Molecular Catalysis", 69 (1991) pp. 95–103 E. Babolov et al.
Draft of 24$^{th}$ Reaction of Synthesis Symposium, p. 68 (1998).
Neftekhimiya, 16(1), p. 114–119 (1976).
Balbolov, E. KH., et. al., "New Routes To Cyclododecanone", Russ. J. Gen. Chem. (1997), 67(6), 921–926.
Chemical Abstract, Col. 85, No. 7, Aug. 16, 1976, Columbus, Ohio–XP00215473.

* cited by examiner

Primary Examiner—Johann Richter
Assistant Examiner—Sikarl A. Witherspoon
(74) Attorney, Agent, or Firm—Morgan, Lewis & Bockius LLP

(57) ABSTRACT

Cyclododecanone and cyclododecanol are produced each in high yield by reacting a epoxycyclododecane compound with hydrogen in the presence of a solid catalyst containing (a) catalytic component including a platinum group metal, (b) a promoter component including a VIII group, IIb group, IIIb group, IVb group, Vb group VIb group or VIIb group element or lanthanoid element or compound of the element, and (c) a carrier supporting the components (a) and (b) thereon.

12 Claims, No Drawings

METHOD OF PRODUCING CYCLODODECANONE AND CYCLODODECANOL

BACKGROUND OF THE INVENTION

1. Field of the Invention

The present invention relates to a method of producing cyclododecanone and cyclododecanol. More particularly, the present invention relates to a method of producing cyclododecanone and cyclododecanol by a catalytic reaction of an epoxycyclododecane compound with hydrogen. Cyclododecanone and cyclododecanol can be easily converted to a lactum compound, lactone compound or a dicarboxylic acid compound by a conventional method and thus are important intermediate materials for producing synthetic resins or fibers of polyamide 12 and polyesters.

2. Description of the Related Art

As a process for producing cyclododecanone and cyclododecanol by a catalytic reaction of epoxycyclododecane compounds with hydrogen, J. Mol. Catal., Vol 169, pp 95–103 (1991) discloses a catalytic hydrogenating reaction of 2-epoxy-5,9-cyclododecadiene with hydrogen. In this reaction of the reference, 1,2-epoxy-5,9-cyclododecadiene is brought into contact with hydrogen in the presence of a palladium-carrying catalyst at a reaction temperature of 90° C. under a hydrogen gas pressure of 1,275 kPa (13 kg/cm$^2$) on gauge, and epoxycyclododecane is produced as a principal reaction product. Cyclododecanol is produced as a by-product in a yield of 4% and no cyclododecanone is produced. Also, the Draft of 24-th Symposium "Development of Reaction and Synthesis, Nov. 5–6, 1998, pp 68, discloses a process of catalytic reaction of 1,2-epoxy-5,9-cyclododecadiene with hydrogen in the presence of a palladium catalyst at room temperature under the ambient atmospheric pressure. In this process, epoxycyclododecane is produced as a principal product, cyclododecanol is produced, as a by-product, in a yield of 5%, and no cyclododecanone is produced.

Further, Neftekhimiya, 16 (1), 114–119 (1976) discloses a catalytic reaction of 1,2-epoxy-5,9-cyclododecadiene with hydrogen in the presence of a palladium-carried catalyst at a reaction temperature of 140° C. under a hydrogen gas pressure of 8,106 kPa (80 atmospheres). In this reaction, epoxycyclododecane was produced in a yield of 49.5%, cyclododecanol in a yield of 33.3%, and cyclododecanone in a yield of 3.4%.

In view of the prior arts, a method enabling both cyclododecanone and cyclododecanol to be produced, each in a satisfactory yield from epoxycyclododecane compounds, has not yet been provided.

SUMMARY OF THE INVENTION

An object of the present invention is to provide a method of producing cyclododecanone and cyclododecanol from epoxycyclododecane compounds with satisfactory yields thereof.

The above-mentioned object can be attained by the method of producing cyclododecanone and cyclododecanol of the present invention, which comprises bringing an epoxycyclododecane compound and hydrogen into contact with each other in the presence of a solid catalyst comprising:

(a) a catalytic component comprising at least one platinum group metal;

(b) a promoter component comprising at least one member selected from the group consisting of VIII group, Ib group, IIb group, IIIb group, IVb group, Vb group, VIb group and VIIb group elements, and lanthanoid elements and compounds of the above-mentioned elements; and (c) a carrier on which the catalytic component and the promoter component are supported, to thereby hydrogenate the epoxycyclododecane compound and produce cyclododecanone and cyclododecanol.

In the method of producing cyclododecanone and cyclododecanol of the present invention, the epoxycyclododecane compound is preferably selected from the group consisting of monoepoxycyclododecadiene, monoepoxycyclododecene and monoepoxycyclododecane.

In the method of producing cyclododecanone and cyclododecanol of the present invention, the promoter component (b) of the solid catalyst preferably comprises at least one member selected from the group consisting of nickel metal, iron metal, copper metal, iron(III) nitrate, iron(III) chloride, iron(II) chloride, iron(II) sulfate, triiron tetraoxide, iron(III) hydroxide, cobalt nitrate, cobalt bromide, cobalt oxide, cobalt hydroxide, nickel nitrate, nickel oxide, nickel hydroxide, copper nitrate, copper acetate, silver oxide, gold hydroxide, yttrium chloride, titanium chloride, vanadium oxide, tungsten oxide, molybdenum oxide, manganese nitrate, rhenium oxide, zinc nitrate, zinc chloride, zinc hydroxide, cadmium nitrate, cadmium oxide, mercury oxide, cerium oxide, samarium chloride, dysprosium chloride, and ytterbium oxide.

In the method of producing cyclododecanone and cyclododecanol of the present invention, the carrier (c) of the solid catalyst preferably comprises an inert inorganic material selected from the group consisting of activated carbon, α-alumina, γ-alumina, silica, silica-alumina, titania, zeolite and spinel.

In the method of producing cyclododecanone and cyclododecanol of the present invention, the catalytic component (a), for the solid catalyst is preferably present in an amount of 0.01 to 20% by weight, based on the weight of the inert carrier.

In the method of producing cyclododecanone and cyclododecanol of the present invention, the metal atomic ratio (a)/(b) of the catalytic component (a) to the promoter component (b) for the solid catalyst is preferably 10,000:1 to 1:4.

In the method of producing cyclododecanone and cyclododecanol of the present invention, the solid catalyst is preferably present in a molar amount, in terms of the platinum group metal, of 0.00001 to 0.1 times the molar amount of the epoxycyclododecane compound.

In the method of producing cyclododecanone and cyclododecanol of the present invention, the hydrogenation reaction of the epoxycyclododecane compound with hydrogen in the presence of the solid catalyst is preferably carried out at a reaction temperature of 60 to 250° C. under a hydrogenr gas pressure of 98 to 14,710 kPa on gauge.

In the method of producing cyclododecanone and cyclododecanol of the present invention, the hydrogenation reaction of the epoxycyclododecane compound with hydrogen is preferably carried out in an organic liquid medium comprising at least one member selected from the group consisting of n-hexane, n-heptane, n-tetradecane, cyclohexane, tetrahydrofuran, dioxane, methyl alcohol, ethyl alcohol, tertiary butyl alcohol, tertiary amyl alcohol, ethyl acetate and butyl acetate.

In the method of producing cyclododecanone and cyclododecanol of the present invention, the liquid medium is preferably employed in an amount not exceeding 20 times the weight of the epoxycyclododecane compound.

In the method of producing cyclododecanone and cyclododecanol of the present invention, the platinum group metal is preferably palladium.

In the method of producing cyclododecanone and cyclododecanol of the present invention, the promoter for catalyst preferably comprises at least one member selected from the group consisting of VIII group, Ib group and IIb group elements, lanthanoid elements, and compounds of the elements.

DESCRIPTION OF THE PREFERRED EMBODIMENTS

In the method of the present invention, an epoxycyclododecane compound and hydrogen are brought into contact with each other in the presence of a specific solid catalyst, to produce cyclododecanone and cyclododecanol.

The epoxycyclododecane compound usable as a starting material for the method of the present invention is defined as an organic compound constituted from a saturated or unsaturated 12-membered cyclic hydrocarbon structure and an epoxy group attached to the cyclic hydrocarbon structure. The epoxycyclododecane compound for the method of the present invention is preferably selected from the group consisting of epoxycyclododecadiene, epoxycyclododecene, and epoxycyclododecane. In the above-mentioned epoxycyclododecane compounds, the epoxy ring structure and double bond structure may be of cis-type of trans type, or of other any type.

The epoxycyclododecane compound subjected to the method of the present invention may be in a trade-available grade or a grade refined by a conventional refining means, for example, distillation.

The solid catalyst usable for the method of the present invention comprises the compounds of:

(a) a catalytic component comprising at least one platinum group metal;

(b) a promoter component comprising at least one member selected from the group consisting of VIII group, Ib group. IIb group, IIIb group, IVb group, Vb group, VIb group and VIIb group elements, and lanthanoid elements and compounds of the above-mentioned elements; and (c) a carrier on which the catalytic component and the promoter component are supported, to thereby hydrogenate the epoxycyclododecane compound and produce cyclododecanone and cyclododecanol.

The platinum group metal usable for the catalytic component (a) of the solid catalyst is one of the platinum group elements, for example, ruthenium, rhodium, palladium, osmium, iridium and platinum and is preferably palladium.

The catalyst component (a) is supported together with a promoter component (b) on a carrier (c), preferably a inert carrier to form a solid catalyst for the reaction of the present invention. The promoter component (b) of the solid catalyst comprises at least one member selected from the group as defined above. Each element can be used in the state of a metal or a compound.

Preferably, the promoter (b) for the solid catalyst comprises at least one member selected from the group consisting of VIII group, Ib group and IIb group elements, lanthanoid elements, and compounds of the VIII group, Ib group, IIb group and lanthanoid elements.

The compounds of the above-mentioned elements for the promoter (b) include nitrates, sulfates, organic acid salts, halides, oxides and hydroxides of the above-mentioned elements.

Particularly, the promoter component (b) of the solid catalyst may comprise at least one member selected from the group consisting of nickel metal, iron metal, copper metal, iron(III) nitrate, iron(III) chloride, iron(II) chloride, iron(II) sulfate, triiron tetraoxide, iron(III) hydroxide, cobalt nitrate, cobalt bromide, cobalt oxide, cobalt hydroxide, nickel nitrate, nickel oxide, nickel hydroxide, copper nitrate, copper-acetate, silver oxide, gold hydroxide, yttrium chloride, titanium chloride, vanadium oxide, tungsten oxide, molybdenum oxide, manganese nitrate, rhenium oxide, zinc nitrate, zinc chloride, zinc hydroxide, cadmium nitrate, cadmium oxide, mercury oxide, cerium oxide, samarium chloride, dysprosium chloride, thulium chloride, thulium oxide, and ytterbium oxide.

The carrier (c) for the solid catalyst comprises an inert inorganic material preferably selected from the group consisting of activated carbon, α-alumina, γ-alumina, silica, silica-alumina, titania, zeolite and spinel. More preferably, α-alumina and γ-alumina are employed for the carrier.

In the solid catalyst, the catalytic component (a) comprising at least one platinum group metal is preferably present in an amount of 0.01 to 20% by weight, more preferably 0.1 to 10% by weight, based on the weight of the inert carrier.

The platinum group metal of the catalytic component (a) may be supported on the surface or in the inside of the carrier (c) or on the surface and in the inside of the carrier (c).

In the solid catalyst, the metal atomic ratio (a)/(b) of the catalytic component (a) to the promoter component (b) for the solid catalyst is preferably 10,000:1 to 1:4, more preferably 5,000:1 to 1:3.

In the method of the present invention, the solid catalyst is preferably employed in a molar amount, in terms of the platinum group metal, of 0.00001 to 0.1 time, more preferably 0.00005 to 0.01 time the molar amount of the epoxycyclododecane compound.

In the method of the present invention, the hydrogenation reaction of the epoxycyclododecane compound with hydrogen in the presence of the solid catalyst is preferably carried out at a reaction temperature of 60 to 250° C., more preferably 80 to 230° C. still more preferably 100 to 200° C. under a hydrogen gas pressure of 98 to 14,710 kPa, more preferably 196 to 9,807 kPa, still more preferably 196 to 4,903 kPa on gauge.

When the reaction temperature is too high, a yield of a by-product having a high boiling temperature may unpreferably increase. When the reaction temperature and the hydrogen pressure are too low, the reaction rate, namely the production rate of cyclododecanone and cyclododecanol may undesireably decrease.

In the method of the present invention, the hydrogenation reaction system optionally contains an organic liquid reaction medium. The organic liquid medium preferably comprises at least one member selected from the group consisting of hydrocarbons, for example, n-hexane, n-heptane, n-tetradecane and cyclohexane; ether compounds, for example, tetrahydrofuran and dioxane; aliphatic alcohol compounds, for example, methyl alcohol, ethyl alcohol, tertiary butyl alcohol, and tertiary amyl alcohol; and ester compounds, for example, ethyl acetate and butyl acetate.

These liquid compounds may be employed alone or in a mixture of two or more thereof.

The liquid medium is preferably employed in an amount not exceeding 20 times, more preferably not exceeding 10 times the weight of the epoxycyclododecane compound.

After the hydrogenation reaction of the epoxycyclododecanone compound with hydrogen is completed, the target cyclododecanone and cyclododecanol are easily collected from the reaction mixture by a conventional separating procedure, for example, distillation.

EXAMPLES

The present invention will be further illustrated by the following examples.

Production Examples 1 of Solid Catalyst A mixture solution was prepared by mixing 0.415 g of palladium chloride ($PdCl_2$) and 0.242 g of samarium chloride hexahydrate ($SmCl_3.6H_2O$) with 1.6 g of 10 weight % aqueous hydrochloric acid solution; heating the mixture to a temperature of 70° C. for 30 minutes; and diluting the heated mixture with water to adjust the volume of the mixture solution to 30 ml.

To the mixture solution, 4.75 g of α-alumina particles having an average particle size of 15 μm was added, and the mixture was dried and solidified by evaporating the water at a temperature of 70° C. The dried mixture was mixed with 35 ml of an aqueous solution of 1.8% by weight of sodium hydroxide, and the resultant alkali liquid was stirred at a temperature of 70° C. for 4 hours. The resultant alkali treatment product was centrifuged, washed with ion-exchanged water to such an extent that no chloride ions were detected with silver nitrate, and then dried at a temperature of about 70° C. for one hour.

of metal, supported on an α-alumina carrier. After the autoclave was closed, epoxycyclododecane (ECD) was subjected to a reaction with hydrogen at a temperature of 200° C. under a hydrogen gas pressure of 4,903 kPa on gauge for 2 hours. After the reaction was completed, the autoclave was cooled to room temperature, and the resultant reaction mixture was subjected to analysis.

The analysis was effected by gas chromatography. As a result of the analysis, it was confirmed that the starting epoxycyclododecane (ECD) was completely consumed, and cyclododecanone (CDON) was obtained in a yield of 8.6 molar %, and cyclododecanol (CDOL) in a yield of 88.1 molar %.

Examples 2 to 4 and Comparative Example 1 In each of Examples 2 to 4 and Comparative Example 1, the same reaction and analysis procedures as in Example 1 was carried out except that the solid catalyst of Example 1 was replaced by a solid catalyst having the composition as shown in Table 1. Namely, in the preparation of the solid catalyst samarium chloride hexahydride was replaced by thulium chloride hexahydrate, in Example 2, by ytterbium chloride hexahydrate in Example 3 and by dysprosium chloride hexahydrate in Example 4, and was omitted in Comparative Example 1.

The analysis results are shown in Table 1.

TABLE 1

| Example No. | | Catalyst Catalytic component (a) (wt %) | Catalyst Promoter component (b) (wt %) | Catalyst Metal atom ratio of (b)/(a) | Carrier (c) | Reaction temperature (° C.) | Reaction time (h) | Conversion of ECD (%) | yield (mol %) CDON | yield (mol %) CDOL | yield (mol %) Total |
|---|---|---|---|---|---|---|---|---|---|---|---|
| Example | 1 | Pd 5.0 | Sm 2.0 | 0.28 | α-alumina | 200 | 2 | 100 | 8.6 | 88.1 | 96.7 |
| | 2 | Pd 5.0 | Tm 2.0 | 0.25 | α-alumina | 200 | 2 | 100 | 8.4 | 89.9 | 98.3 |
| | 3 | Pd 5.0 | Yb 2.0 | 0.25 | α-alumina | 200 | 2 | 100 | 9.5 | 88.9 | 98.4 |
| | 4 | Pd 5.0 | Dy 2.0 | 0.26 | α-alumina | 200 | 2 | 100 | 10.3 | 87.3 | 97.6 |
| Comparative Example | 1 | Pd 5.0 | — | — | α-alumina | 200 | 2 | 92 | 19 | 68.9 | 87.9 |

Thereafter, the dried product was suspended in cyclohexane placed in an autoclave, and was subjected to a reduction treatment in a hydrogen gas atmosphere under a hydrogen pressure of 980.1 kPa (10 kg/cm²) on gauge at a temperature of 120° C. for one hour.

A solid catalyst which is in the form of fine particles and in which palladium in an amount of 5% by weight in terms of palladium metal and samarium in an amount of 2% by weight in terms of samarium metal are supported on α-alumina carrier particles in a Pa/Sm atomic ratio of 3.53, was obtained.

Example 1

A SUS autoclave having an inner volume of 100 ml and equipped with a stirrer was charged with 20 g (0.11 mole) of epoxycyclododecane, which will be referred to as "ECD" hereinafter, and 0.4 g of the catalyst produced in Production Example 1 of Solid Catalyst and comprising 5% by weight of palladium and 2% by weight of samarium, each in terms

Example 5

A glass autoclave having an inner volume of 50 ml was charged with 0.5 g (2.81 millimoles) of 1,2-epoxy-5,9-cyclododecadiene, which will be referred to as "ECDE" hereinafter, 2.0 g of a reaction medium consisting of n-tetradecane and 0.1 g of the solid catalyst produced in the same manner as in Production Example 1 of Solid Catalyst except that 5% by weight of palladium and 2% by weight of copper (metallic copper), each in terms of metal were supported on an α-alumina carrier.

In the preparation of the solid catalyst, samarium chloride hexahydrate of Catalyst Production Example 1 was replaced by copper chloride hydrate. After the autoclave was closed, 1,2-epoxy-5,9-cyclododecadiene (ECDE) was subjected to a reaction with hydrogen at a temperature of 160° C. under a hydrogen gas pressure of 490.3 kPa on gauge for one hour. After the reaction was completed, the autoclave was cooled to room temperature, and the resultant reaction mixture was subjected to analysis.

The analysis was effected by gas chromatography. As a result of the analysis, it was confirmed that the starting 1,2-epoxy-5,9-cyclododecadiene (ECDE) was completely consumed, and cyclododecanone (CDON) was obtained in a yield of 64.8 molar %, and cyclododecanol (CDOL) in a yield of 30.4 molar %.

Examples 6 to 8 and Comparative Example 2 In each of Examples 6 to 8 and Comparative Example 2, the same reaction and analysis procedures as in Example 5 was carried out except that the solid catalyst of Example 5 was replaced by a solid catalyst having the composition as shown in Table 2, and the reaction temperature was changed to that shown in Table 2. Namely, in the preparation of the solid catalyst, samarium chloride hexahydrate of Catalyst Production Example 1 was replaced by cobalt chloride hexahydrate, in Example 6, by nickel chloride hexahydrate in Example 7 and by iron(III) chloride hexahydrate in Example 8, and was omitted in Comparative Example 1.

The analysis results are shown in Table 2.

weight of palladium and 0.5% by weight of iron, each in terms of metal, supported on an γ-alumina carrier. After the autoclave was closed, epoxycyclododecane (ECD) was subjected to a reaction with hydrogen at a temperature of 160° C. under a hydrogen gas pressure of 490.3 kPa on gauge for 2 hours. After the reaction was completed, the autoclave was cooled to room temperature, and the resultant reaction mixture was subjected to analysis.

The analysis was effected by gas chromatography. As a result of the analysis, it was confirmed that the starting epoxycyclododecane (ECD) was completely consumed, and cyclododecanone (CDON) was obtained in a yield of 39.8 molar %, and cyclododecanol (CDOL) in a yield of 57.7 molar %.

Examples 10 and 11

In each of Examples 10 and 11, the same reaction and analysis procedures as in Example 9 was carried out except that the solid catalyst of Example 9 was replaced by a solid

TABLE 2

| Example | | Catalyst | | | | Reaction conditions | | Reaction products | | | |
|---|---|---|---|---|---|---|---|---|---|---|---|
| | | Catalytic component (a) | Promoter component (b) | Metal atom ratio of | | Reaction temperature | Reaction time | Conversion of ECDE | yield (mol %) | | |
| No. | | (wt %) | (wt %) | (b)/(a) | Carrier (c) | (° C.) | (h) | (%) | CDON | CDOL | Total |
| Example | 5 | Pd 5.0 | Cu 2.0 | 0.67 | α-alumina | 160 | 1 | 100 | 64.5 | 30.4 | 95.2 |
| | 6 | Pd 5.0 | Co 2.0 | 0.72 | α-alumina | 130 | 1 | 100 | 35.4 | 59.4 | 94.8 |
| | 7 | Pd 5.0 | Ni 2.0 | 0.73 | α-alumina | 120 | 1 | 100 | 44 | 48.9 | 92.9 |
| | 8 | Pd 5.0 | Fe 0.5 | 0.19 | α-alumina | 140 | 1 | 100 | 52.8 | 40.6 | 93.4 |
| Comparative Example | 2 | Pd 5.0 | — | — | α-alumina | 160 | 1 | 100 | 71.4 | 14.5 | 85.9 |

Example 9

A glass autoclave having an inner volume of 50 ml was charged with 1.0 g (5.5 millimoles) of epoxycyclododecane (ECD), and 0.02 g of a solid catalyst produced in the same manner as in Catalyst Production Example 1 except that samarium chloride hexahydrate was replaced by iron(III) chloride hexahydrate and the catalyst comprised 5% by catalyst having the composition as shown in Table 1. Namely, in the preparation of the solid catalyst in the same manner as in Example 9, γ-alumina for the carrier was replaced by carbon in Example 10, and palladium chloride was replaced by platinum chloride and γ-alumina was replaced by carbon in Example 11.

The analysis results are shown in Table 3.

TABLE 3

| Example | | Catalyst | | | | Reaction conditions | | Reaction products | | | |
|---|---|---|---|---|---|---|---|---|---|---|---|
| | | Catalytic component (a) | Promoter component (b) | Metal atom ratio of | | Reaction temperature | Reaction time | Conversion of ECD | yield (mol %) | | |
| No. | | (wt %) | (wt %) | (b)/(a) | Carrier (c) | (° C.) | (h) | (%) | CDON | CDOL | Total |
| Example | 9 | Pd 5.0 | Fe 0.5 | 0.19 | γ-alumina | 160 | 2 | 100 | 39.8 | 57.7 | 97.5 |
| | 10 | Pd 5.0 | Fe 0.5 | 0.19 | carbon | 160 | 2 | 100 | 42.4 | 53.0 | 95.4 |
| | 11 | Pt 5.0 | Fe 0.5 | 0.35 | carbon | 160 | 2 | 100 | 19.0 | 71.3 | 90.3 |

The method of the present invention enables both cyclododecanone and cyclododecanol to be produced at high yields from epoxycyclododecane compounds.

What is claimed is:

1. A method of producing cyclododecanone and cyclododecanol, comprising contacting an epoxycyclododecane compound and hydrogen in the presence of a solid catalyst comprising:
   (a) a catalytic component comprising at least one platinum group metal;
   (b) a promoter component comprising at least one member selected from the group consisting of VIII group, Ib group, IIb group, IIIb group, IVb group, Vb group, VIb group and VIIb group elements, lanthanoid elements and compounds of the above-mentioned elements; and
   (c) a carrier on which the catalytic component and the promoter component are supported,
to thereby hydrogenate the epoxydodecane compound and produce cyclododecanone and cyclododecanol.

2. The method of producing cyclododecanone and cyclododecanol as claimed in claim 1, wherein the epoxycyclododecane compound is selected from the group consisting of monoepoxycyclododecadiene, monoepoxycyclododecene and monoepoxycyclododecane.

3. The method of producing cyclododecanone and cyclododecanol as claimed in claim 1, wherein the promoter component (b) of the solid catalyst comprises at least one member selected from the group consisting of nickel metal, iron metal, copper metal, iron(III) nitrate, iron(III) chloride, iron(II) chloride, iron(II) sulfate triiron tetraoxide, iron(III) hydroxide, cobalt nitrate, cobalt bromide, cobalt oxide, cobalt hydroxide, nickel nitrate, nickel oxide, nickel hydroxide, copper nitrate, copper acetate, silver oxide, gold hydroxide, yttrium chloride, titanium chloride, vanadium oxide, tungsten oxide, molybdenum oxide, manganese nitrate, rhenium oxide, zinc nitrate, zinc chloride, zinc hydroxide, cadmium nitrate, cadmium oxide, mercury oxide, cerium oxide, samarium chloride, dysprosium chloride, thulium chloride, thulium oxide, and ytterbium oxide.

4. The method of producing cyclododecanone and cyclododecanol as claimed in claim 1, wherein the carrier (c) of the solid catalyst comprises an inert inorganic material selected from the group consisting of activated carbon, α-alumina, γ-alumina, silica, silica-alumina, titania, zeolite and spinel.

5. The method of producing cyclododecanone and cyclododecanol as claimed in claim 1, wherein the catalytic component (a) for the solid catalyst is present in an amount of 0.01 to 20% by weight, based on the weight of the inert carrier.

6. The method of producing cyclododecanone and cyclododecanol as claimed in claim 1, wherein the catalytic component (a) and the promoter component (b) for the solid catalyst exist in a metal atomic ratio (a)/(b) of 10,000:1 to 1:4.

7. The method of producing cyclododecanone and cyclododecanol as claimed in claim 1, wherein the solid catalyst is present in a molar amount, in terms of the platinum group metal, of 0.00001 to 0.1 time the molar amount of the epoxycyclododecane compound.

8. The method of producing cyclododecanone and cyclododecanol as claimed in claim 1, wherein the method is carried out at a reaction temperature of 60 to 250° C. under a hydrogen gas pressure of 98 to 14,710 kPa on gauge.

9. The method of producing cyclododecanone and cyclododecanol as claimed in claim 1, wherein the method is carried out in an organic liquid medium comprising at least one member selected from the group consisting of n-hexane, n-heptane, n-tetradecane, cyclohexane, tetrahydrofuran, dioxane, methyl alcohol, ethyl alcohol, tertiary butyl alcohol, tertiary amyl alcohol, ethyl acetate and butyl acetate.

10. The method of producing cyclododecanone and cyclododecanol as claimed in claim 9, wherein the organic liquid medium is employed in an amount not exceeding 20 times the weight of the epoxycyclododecane compound.

11. The method of producing cyclododecanone and cyclododecanol as claimed in claim 1, wherein the platinum group metal is palladium.

12. The method of producing cyclododecanone and cyclododecanol as claimed in claim 1, wherein the promoter component comprises at least one member selected from the group consisting of VIII group, Ib group and IIb group elements, lanthanoid elements, and compounds of the above-mentioned elements.

* * * * *